United States Patent [19]

Umansky et al.

[11] Patent Number: 5,510,558
[45] Date of Patent: Apr. 23, 1996

[54] OXIDATIVE DEHYDROGENATION OF HYDROCARBONS WITH ACTIVE CARBON CATALYST

[75] Inventors: Benjamin S. Umansky, Wilmington, Del.; Kevin A. Boyer, Marcus Hook; Chao-Yang Hsu, Media, both of Pa.

[73] Assignee: Sun Company, Inc. (R&M), Philadelphia, Pa.

[21] Appl. No.: 174,731

[22] Filed: Dec. 29, 1993

[51] Int. Cl.$^6$ .................................................. C07C 5/32
[52] U.S. Cl. .................... 585/658; 585/660; 585/662; 585/663; 585/621; 585/443
[58] Field of Search ........................... 585/622, 440, 585/654, 658, 660, 661, 662, 663, 621, 618, 623, 624, 625, 627, 443

[56] References Cited

U.S. PATENT DOCUMENTS 3,113,984  12/1963  Gosselin et al. .
3,497,564  2/1970   Allen et al. .
3,725,494  4/1973   Ripley .
4,652,690  3/1987   Lee .......................................... 585/443

OTHER PUBLICATIONS

Alkhazov et al., "Oxidative Dehydrogenation of Alkyl Aromatic Hydrocarbons on Aluminum Oxide Catalysts 1. The Nature of The Process of Oxidative Dehydrogenation of Ethylbenzene on Aluminum Oxide", *Kinetika i. Kataliz*, vol. 13, No. 2, 509–512 (1972) (English version only, pp. 460–462).

*Primary Examiner*—Asok Pal
*Assistant Examiner*—Bekir L. Yildirim
*Attorney, Agent, or Firm*—Q. Todd Dickinson; Stephen T. Falk

[57] ABSTRACT

Oxidative dehydrogenation of alkanes and alkylaromatic hydrocarbons is achieved by contact with an active carbon catalyst. In various aspects of the invention, the oxidative dehydrogenation is performed at a pressure above about 100 psia, and/or at a temperature in the range from about 500° C. to about 800° C., and/or the active carbon catalyst contains a metal, for example, molybdenum.

10 Claims, No Drawings

OXIDATIVE DEHYDROGENATION OF HYDROCARBONS WITH ACTIVE CARBON CATALYST

BACKGROUND OF THE INVENTION

The conventional processes for production of lower olefins by catalytic dehydrogenation of alkanes face a number of technical challenges, because of their endothermicity, thermodynamic limitations and rapid catalyst deactivation due to deposition of coke on the catalyst. At the same time, the use of oxidative dehydrogenation for lower alkanes is attracting increasing interest, both because of energetic and thermodynamic advantages—the exothermicity of the process and absence of equilibrium limitations and the stability of the catalyst—little or no deactivation. Although oxidative dehydrogenation usually involves the use of a catalyst, and is therefore literally a catalytic dehydrogenation, oxidative dehydrogenation is distinct from what is normally called "catalytic dehydrogenation" in distinct from what is normally called "catalytic dehydrogenation" in that the former involves the use of an oxidant, and the latter does not. In the subsequent disclosure, "oxidative dehydrogenation", though employing a catalyst, will be understood as distinct from so-called "catalytic dehydrogenation" processes in that the latter do not involve the interaction of oxygen in the feed with the hydrocarbon feed.

PRIOR ART

Carbon molecular sieves, also known as active or activated carbons, are a class of substances which have been proposed for use as catalysts for oxidative dehydrogenation of alkanes. In the following disclosure, the term "active carbon" will be used to designate this class of substances, and will be understood to include what are called by other names such as "carbon molecular sieve".

The Lee and Gosselin et al references below disclose active carbon as catalyst for oxidative dehydrogenation of alkylaromatics (Lee) or of alkanes (Gosselin et al).

The Lee reference, namely C. S. Lee U.S. Pat. No. 4,652,690, issued Mar. 24, 1987, discloses that carbon molecular sieves are catalysts for oxidative dehydrogenation of ethylbenzene to styrene in the presence of oxygen and steam at temperatures of 300° to 400° C. and unspecified pressure.

The Gosselin et al reference, namely K. F. Gosselin et al U.S. Pat. No. 3,113,984, issued Dec. 10, 1963, discloses that activated carbons are catalysts for oxidative dehydrogenation of alkanes at 900° F. to 950° F. and unspecified pressure. Since the reaction was done in a Pyrex tube without a back pressure regulator, atmospheric or lower pressure was apparently used.

In addition to active carbon, aluminum oxide has been used as a catalyst for oxidative dehydrogenation of hydrocarbons, in T. G. Alkhazov et al, "Oxidative Dehydrogenation of Alkyl Aromatic Hydrocarbons on Aluminum Oxide Catalysts 1. The Nature of the Process of Oxidative Dehydrogenation of Ethylbenzene on Aluminum Oxide", *Kinetica i Kataliz.*, Vol. 14, No. 5, pp 1182–1188 (1973); this reference discloses that aluminum oxide is a catalyst for oxidative dehydrogenation of ethylbenzene to styrene in the presence of air at temperature of 500° C. and subatmospheric, e.g. 10 torr., pressure. Coke formed during the oxidative dehydrogenation reaction is disclosed as possessing some catalytic activity.

DESCRIPTION OF THE INVENTION

This invention provides processes for oxidative dehydrogenation of alkanes to olefins, using active carbon catalysts, with or without added metals.

In one embodiment of the invention, alkanes are oxidatively dehydrogenated using active carbon as catalyst in a process in which superatmospheric pressure is used, in order to provide superior results to those obtained with atmospheric pressure. This embodiment may also be applied to the oxidative dehydrogenation of alkylaromatic hydrocarbons.

In another embodiment, alkanes are oxidatively dehydrogenated using active carbon as catalyst at temperatures in the range from about 500° F. to about 800° F. This embodiment provides advantages over prior art processes using higher temperatures.

In another embodiment, alkanes are oxidatively dehydrogenated using an active carbon catalyst with added metals as subsequently more fully disclosed.

OXIDATIVE DEHYDROGENATION WITH ACTIVE CARBON CATALYSTS AT ELEVATED PRESSURE

In one embodiment of the invention, a novel process for oxidative dehydrogenation of hydrocarbons is provided in which an active carbon catalyst is employed, and the process is performed at a pressure of at least about 100 psia.

The use of elevated pressure in this embodiment of the invention provides superior results in the use of active carbon catalysts to those obtained at lower pressures.

Typically, in this embodiment, the alkane feedstock together with an oxidant is passed through a fixed bed reactor containing a catalyst under reaction conditions to give olefins, carbon oxides and water. The oxidant may be oxygen, air or other oxygen-containing mixtures. Sulfur dioxide, hydrogen sulfide and steam together with oxygen or oxygen/nitrogen mixtures also can be used. The reaction temperature is typically between about 500° F. and about 800° F., more preferably between about 600° F. and about 700° F. The reaction pressure, as previously stated, is higher than about 100 psia, and is preferably in the range of from about 200 psia and about 400 psia.

OXIDATIVE DEHYDROGENATION WITH ACTIVE CARBON CATALYST IN PARTICULAR TEMPERATURE RANGE

In this embodiment, alkanes are oxidatively dehydrogenated using active carbon catalyst at a temperature in the range from 600° F. and 800° F. Good results are obtained as shown in Example I while avoiding the expense of the higher temperatures used in the Gosselin et al patent above wherein temperatures of 900° F. to 950° F. are used in oxidative dehydrogenation of alkanes with active carbon as catalyst.

OXIDATIVE DEHYDROGENATION WITH ACTIVE CARBON CATALYST CONTAINING ADDED METAL

The catalyst used in the oxidative dehydrogenation according to this embodiment of the invention comprises active carbon and an added metal.

The metal which is used in the catalysts according to this embodiment of the invention is a Group VB, VIB, VIIB, VIII, IIB, IIIA, IVA or VA metal, such as molybdenum, vanadium, chromium, manganese, iron, zinc, cobalt, tin, lead, gallium, antimony, tungsten or nickel. The catalyst may contain more than one metal.

The following examples illustrate the invention:

EXAMPLE 1

This example illustrates the embodiment of the invention in which oxidative dehydrogenation of alkanes is performed at an elevated pressure, using an active carbon catalyst without added metal.

In this example, isobutane was dehydrogenated using an active carbon catalyst, designated "Carbon Molecular Sieve, AX 21", by its supplier, Anderson Development Company. 5 ml of the catalyst were placed in a ½" O.D. reactor tube. After drying the catalyst with nitrogen flowing at 100 ml/min for 10 hr, isobutane was pumped into the reactor at 11.3 ml/hr and a gas stream of 4% oxygen in nitrogen at 6000 ml/hr was used to replace the nitrogen flow. The reactor pressure was adjusted to 240 psia with a back pressure regulator and the reaction products were analyzed using an on-line GC. The results obtained at temperature of 698° F. and 752° F. are shown in Table I.

TABLE I

| CATALYST: | AX21 | AX21 |
|---|---|---|
| LHSV (1/Hr) | 3 | 3 |
| GHSV [$O_2/N_2$(4% $O_2$)] (1/Hr): | 2000 | 2000 |
| TEMPERATURE (F.): | 698 | 752 |
| PRESSURE (psia): | 240 | 240 |
| i-$C_4H_{10}$ CONVERSION (MOL %) | 25 | 20 |
| SELECTIVITY TO i-$C_4H_8$ (%): | 40 | 38 |
| SELECTIVITY TO $C_3H_6$ | 25 | 18 |
| SELECTIVITY TO $CO_x$ (%): | 20 | 31 |
| SELECTIVITY TO $C_4^+$ (%) | 10 | 7 |
| SELECTIVITY TO $C_4^-$ (%) | 5 | 6 |

EXAMPLE 2

In this example of operation according to the invention, isobutane was oxidatively dehydrogenated using an active carbon catalyst impregnated with molybdenum.

The procedure in Example 2 was the same as in Example 1, except using the "Carbon Molecular Sieve" containing 10% molybdenum. The catalyst was prepared by impregnation procedure (4 g Of $MoO_3$ on 26 g of dried AX21 catalyst). The reaction conditions and results are shown in Table II.

TABLE II

| CATALYST: | AX21/10% Mo | AX21/10% Mo |
|---|---|---|
| LHSV (1/Hr): | 4 | 4 |
| GHSV [$O_2/N_2$ (4% $O_2$)] | 2000 | 2000 |
| TEMPERATURE (F.): | 660 | 698 |
| PRESSURE (psia): | 300 | 300 |
| i-$C_4H_{10}$ CONVERSION (MOL %): | 26 | 32 |
| SELECTIVITY TO i-$C_4H_8$ (%): | 41 | 39 |
| SELECTIVITY TO $C_3H_6$ (%): | 28 | 30 |
| SELECTIVITY TO $CO_x$ (%) | 12 | 12 |
| SELECTIVITY TO $C_4^-$ (%) | 7 | 9 |
| SELECTIVITY TO $C_4^+$ (%) | 12 | 10 |

The active carbon which is used in the various embodiments of the invention has a pore structure which is known in the art to have catalytic effect in oxidative dehydrogenation processes. The novelty in the various embodiments of the invention is the use of active carbon having such pore size in combination with other elements, such as the pressure and/or the temperature of the oxidative dehydrogenation process, and/or the presence of added metals in the active carbon catalyst. Preferably, the active carbon used in the various embodiments of the invention has pores at least 10 percent of which, have size between about 3 and about 20 Angstroms.

The invention claimed is:

1. Process for oxidative dehydrogenation of alkanes which comprises contacting an alkane and oxygen with active carbon at a pressure of at least about 100 psia.

2. Process according to claim 1 in which said pressure is in the range from about 200 psia to about 400 psia.

3. Process for oxidative dehydrogenation of alkanes which comprises contacting an alkane and oxygen with active carbon at a temperature in the range from about 500° F. to about 800° F.

4. Process according to claim 3 wherein said temperature is in the range from about 600° F. to about 700° F.

5. Process for oxidative dehydrogenation of alkanes or alkyalaromatic hydrocarbons which comprises contacting an alkane or alkylaromatic hydrocarbon with oxygen and a catalyst comprising active carbon and an added metal under oxidative dehydrogenation conditions.

6. Process according to claim 5 wherein said metal is selected from the group consisting of Groups VB, VIB, VIIB, VIII, IIB, IIIA, IVA and VA of the Periodic Table.

7. Process according to claim 6 wherein said metal is selected from the group consisting of molybdenum, vanadium, chromium, manganese, iron, zinc, cobalt, tin, lead, gallium, antimony, tungsten and nickel.

8. Process according to claim 7 wherein said metal is molybdenum.

9. Process according to claim 1, claim 3 or claim 5 in which said active carbon has pores at least 10 percent of which have size between about 3 and about 20 Angstroms.

10. Process according to claim 9 in which between about 25 and about 100 percent of said pores of said active carbon have said size.

* * * * *

UNITED STATES PATENT AND TRADEMARK OFFICE
CERTIFICATE OF CORRECTION

PATENT NO. : 5,510,558
DATED : April 23, 1996
INVENTOR(S) : Benjamin Umansky
　　　　　　　　Kevin A. Boyer
　　　　　　　　Chao-Yang Hsu It is certified that error appears in the above-indentified patent and that said Letters Patent is hereby corrected as shown below:

In The Claims:

Delete claims 1 through 4 inclusive.

Renumber Claim 5 as -- 1 --

Renumber Claim 6 as -- 2 --; and delete "claim 5" and insert -- claim 1 --

Renumber Claim 7 as -- 3 --; and delete "claim 6" and insert -- claim 2 --

Renumber Claim 8 as -- 4 --; and delete "claim 7" and insert -- claim 3 --

Renumber Claim 9 as -- 5 --; and delete "claim 1, claim 3 or claim 5" and insert -- claim 1 --

Renumber Claim 10 as -- 6 --; and delete "claim 9" and insert -- claim 5 --

Signed and Sealed this

Twenty-eighth Day of October, 1997

Attest:

BRUCE LEHMAN

Attesting Officer　　　　Commissioner of Patents and Trademarks